US006296846B1

(12) United States Patent
Sachs et al.

(10) Patent No.: US 6,296,846 B1
(45) Date of Patent: Oct. 2, 2001

(54) INDUCED TOLERANCE TO XENOGRAFTS

(75) Inventors: David H. Sachs, Newton; A. Benedict Cosimi, Weston; Megan Sykes, Charlestown, all of MA (US)

(73) Assignee: The General Hospital, Massachusetts ( * ) Notice: Subject to any disclaimer, the term of this patent is extended or adjusted under 35 U.S.C. 154(b) by 0 days.

(21) Appl. No.: 08/451,210

(22) Filed: May 26, 1995

Related U.S. Application Data

(63) Continuation of application No. 07/838,595, filed on Feb. 19, 1992, now abandoned, which is a continuation-in-part of application No. 07/817,761, filed on Jan. 8, 1992, now abandoned.

(51) Int. Cl.[7] .................... A61K 48/00; A61K 39/395

(52) U.S. Cl. ................ 424/93.21; 424/93.1; 424/93.7; 424/130.1; 424/577; 424/579

(58) Field of Search ................... 424/93.1, 93.3, 424/93.7, 577, 579, 93.21

(56) References Cited

U.S. PATENT DOCUMENTS

| | | | |
|---|---|---|---|
| 4,772,552 | 9/1988 | Hercend et al. | 435/7.24 |
| 5,087,570 | * 2/1992 | Weisman et al. | 435/240.1 |
| 5,160,490 | * 11/1992 | Naughton et al. | 435/284 |

FOREIGN PATENT DOCUMENTS 0 341 966 A2   11/1989   (EP).

OTHER PUBLICATIONS

Kaufman et al. (1995) Annu. Rev. Immunol., vol. 13; 339–367, 1995.*
Sablinski et al. (1997) Surgery, vol. 121; 381–391, 1997.*
D.H. Sachs(1993) Ann. Thorac. Surg., vol. 56; 1221–1227, 1993.*
Sharabi et al. (1990) J. Exp. Med., vol. 172;195–202, 1990.*
Ildstad et al. (1992) Transplantation, vol. 53, 815–822, 1992.*
Salaün, J., et al. (1990) *Science* 242: 1421–24.*
Okhi, H., et al. (1987) *Science* 237: 1032–35.*
Anklesaria, P., et al. (1987) Proc. Natl. Acad. Sci. USA 84: 7681–85.*
Aksentijevich I. et al. (1991) "Natural Antibodies Can Inhibit Bone Marrow Engraftment in the Rat →Mouse Species Combination" *J. of Immunology*, 147(12):4140–4146.
Anklesaria et al. (1987) "Engraftment of a Clonal Bone Marrow Stromal Cell Line In Vivo Stimulates Hematopoietic Recovery From Total Body Irradiation" *PNAS* 84:7681–7685.
Auchincloss, H., Mechanisms and control of xenograft rejection (mice, monkeys, swine), Federal Research in Progress, I.D. No.:5ro1HL36372–05.

Barber W. H. et al. (1991) "Long–Term Results of a Controlled Prospective Study With Transfusion of Donor–Specific Bone Marrow In 57 Cadaveric Renal Allograft Recipients" *Transplantation*, 51(1):70–75.
Billingham, R.E. et al. (1953) "Actively acquired tolerance' of foreign cells" *Nature* 172:603–606.
Cooper, D.K.C. et al. (1988) "Effects of cyclosporine and antibody adsorption on pig cardiac xenograft survival in the baboon" *The Journal of Hart Transplantation*, 7:238–246.
Cosimi, A.B. et al. (1970) "Experience with large–dose intravenous antithymocyte globulin in primates and man" *Surgery* 68(1):54–61.
Dalmasso, A.P. Inhibition of complement activation in xenotransplantation, Federal Research in Progress. I.D. No.: 0003; 73094; 618.
Fiedler, L. et al. (1974) "Experimental xenografting in widely divergent species. Modification of the hyperacute xenogeneic rejection of kidneys from pigs by extreme hemodilution of dogs" *W. Res Exp. Med.* 163:137–153.
Fischel, R.J. et al. (1991) "Prolonged survival of a discordant cardiac xenograft in a rhesus monkey" *Transplantation Proceedings*, 23:589–590.
Fischel R. J. et al. (1990) "Removal of IgM anti–endothelial antibodies results in prolonged cardiac xenograft survival" *Transplantation Proceedings* 22:1077–1078.
Gustaffson et al. (1990) "Structure of Miniature Swine Class II DRB genes: Conservation of Hypervariable Amino Acid Residues Between Distantly Related Mammalian Species" *Proc. Natl. Acad. Sci. USA* 87:9798–9802.
Guzzetta, P.C. (1991) "Induction of kidney transplantation tolerance across major histocompatibility complex barriers by bone marrow transplantation in miniature swine" *Transplantation* 51(4):862–866.
Hammer, C. et al. (1973) "Performed natural antibodies in animals and man" *Europ. Surg. Res.* 5:162–166.
Hirsch et al. (1990) "Class II genes of Miniature Swine" *Immunogenetics* 31:52–56.

(List continued on next page.)

Primary Examiner—Bruce R. Campell
Assistant Examiner—Anne Marie S. Beckerleg
(74) Attorney, Agent, or Firm—Fish & Richardson P.C.

(57) ABSTRACT

The invention features a method designed to lengthen the time an implanted organ (a xenograft) survives in a xenogeneic host prior to rejection. Preparation of the recipient for transplantation includes the following steps: First, the recipient is administered low dose radiation. Second, an antibody preparation that binds T cells and NK cells is injected into the recipient. Third, natural antibodies are absorbed from the recipient's blood by hemoperfusion of an organ of the donor species. Fourth, hematopoietic stromal tissue of the donor species is administered to the recipient. Fifth, donor hematopoietic stem cells are injected into the recipient. Finally, the xenograft organ is implanted into the recipient mammal. Best results are obtained when all steps are used in combination.

24 Claims, No Drawings

OTHER PUBLICATIONS

Ildstad, S.T. et al. (1984) "Reconstitution with syngeneic plus allogeneic or xenogeneic bone marrow leads to specific acceptance of allografts or xenografts" *Nature* 307(5947):168–170.

Krowka, J.F. (1991) *J. of Immunology* 146:3751–3756.

Lubin, I. (1991) *Science* 252:427–431.

Mayumi, H. et al. (1989) "Long lasting skin allograft tolerance in adult mice induced across fully allogenic (multimajor H–2 plus multiminor histocompatibility) antigen barriers by a tolerance–inducing method using cyclophosphamide" *J. Exp. Med.* 169:212–238.

McCune, J.M. (1988) *Science* 241:1632–1639.

McDuffie, M. et al. (1988) "Involvement of major histocompatibility complex products in tolerance induction in the thymus" *The Journal of Immunology* 141:1840–1847.

Miyake, K. (1991) *J. of Exp. Med.* 173:599–607.

Myburth et al (1984) "Total Lymphoid Irradiation In Kidney And Liver Transplantation In The Baboon: Prolonged Graft Survival And Alterations In T Cell Subsets With Low Cumulative Dose Regimens" *The Journal of Immunology*, 132(2):1019–1025.

Namikawa, R. (1990) "Long Term Human Hematopoiesis in the SCID–hu Mouse" *J. Exp. Med.* 172:1055–1063, especially the abstract and page 1060, final paragraph.

Nathan, D.G. Hematopoiesis Following bone Marrow Transplantation (Macaques) ID No. 5P01CA39542–07 Federal Research in Progress.

O'Reilly, R.J. et al. (1985) "Transplantation of marrow–depleted T cells by soybean lectin agglutination and E–rosette depletion: Major histocompatibility complex–related graft resistance in leukemic transplant recipients" *Transplantation Proceedings* 17:455–459.

Pennington, L.R. et al. (1988) "Bone Marrow Transplantation in Miniature Swine" *Transplantation* 45:21–26.

Pescovitz et al. (1984) "Effect of Class II Antigen Matching on Renal Allograft Survival In Miniature Swine" *J. Exp. Med.* 160:1495–1508.

Platt, J.L. et al. (1990) "An Elisa Assay for Xenoreactive Natural Antibodies" *Transplantation* 49:1000–1001.

Platt, J.L. et al. (1991) FASEB. 75th Annual Meeting. Abstracts No. 7761. "Natural Antibodies and the classical complement pathway mediate hyperacute xenograft rejection in pig to primate combination" p. A1707.

Platt, J. L. et al. (1990) "Transplantation of Discordant Xenografts: A review of progress" *Immunology Today* 11(12):451–456.

Platt J.L. et al. (1991) "Immunopathy of hyperacute xenograft rejection in a swine–to–primate model" Transplantation 52:214–220.

Pratt et al. (1990) "Class II genes of Miniature Swine" *Immunogenetics* 31:1–6.

Rayfield et al. (1983) "Tolerance, Immunocompetence, And Secondary Disease In Fully Allogeneic Radiation Chimeras" *Transplantation*, vol. 36: 183–189, No. 2.

Rodt et al. "Antilymphocytic Antibodies and Marrow transplantation. III. Effect of Heterologous Anti–Brain Antibodies on Acute Secondary Disease in Mice" *European J. of Immunology.* 4:25–29, especially the abstract and p. 25, column 1.

Sachs et al. (1988) "Class II genes of Miniature Swine" *Immunogenetics* 28:22–29.

Salavn J. et al. (1990) *Science* 247:1471–74.

Schilling, A. et al. (1975) "Experimental Xenografting in Widely Divergent Species: Interaction of Humoral Factors In Hyperacute Xenograft Rejection in the Rat—Dog System" (author's translation) *Res Exp. Med* 165:79–92.

Sharabi, Y. et al. (1990) "Specific Tolerance Induction Across a Xenogenic Barrier: Production of Mixed Rat Mouse Lymphohematopoietic Chimeras Using A Nonlethal Preparative regimen" The *J. of Exp. Med.* 172:195–202.

Slapak, M. et al. (1971) "Effect of Heparin, Arvin, Liver Perfusion, and Heterologous Antiplatelet serum on refection of pig kidney by dog" *Transplantation Proceedings* 3:558–561.

Soderling, C. (1985) "A Correlation Between Conditioning and Engraftment in Recipients of MHC–mismatched T–Cell–Depleted Murine Bone Marrow Transplants" *J. of Immunology* 135:941–946.

Sykes, M. et al. (1988) "Mixed allogeneic Chimerism as an Approach to Transplantation Tolerance" *Immunology Today* 9:23–27.

Thomas et al. (1991) "Veto Cells Induce Long–Term Kidney Allograft Tolerance In Primates Without Chronic Immunosuppression" *Transplantation Proceedings,* vol. 23(1):11–13.

Thomas et al.(1989) "Promotion of Incompatible Allografts Acceptance In Rhesus Monkeys Given Posttransplant Antithymocyte Globulin And Donor Bone Marrow" *Transplantation*, vol. 47(2):209–215.

Waldman, H. (1989) "Manipulation of T–Cell Responses With Monoclonal Antibodies" *Ann. Re. Immunol.* 7:407–444.

Wee et al. (1992) "The Effects Of OKT4A Monoclonal Antibody On Cellular Immunity Of Nonhuman Primate Renal Allograft Recipients" *Transplantation*, 53(3): 501–507.

Williams, D.A. (1991) *Nature* 352:438–441.

Barber, W. H. et al., "Long–Term Results of a Controlled Prospective Study With Transfusion of Donor–Specific Bone Marrow In 57 Cadaveric Renal Allograft Recipients" *Transplantation*, vol. 51:70–75, No. 1, Jan. 1991.

Aksentijevich I. et al., "Natural Antibodies Can Inhibit Bone Marrow Engraftment in the Rat→Mouse Species Combination" *J. of Immunology*, vol. 147:4140–4146, No. 12, Dec. 1991.

Myburth et al, "Total Lymphoid Irradiation In Kidney And Liver Transplantation In The Baboon: Prolonged Graft Survival And Alterations In T Cell Subsets With Low Cumulative Dose Regimens" *The Journal of Immunology*, vol. 132: 1019–1025, No. 2, Feb. 1984.

Wee et al., "The Effects Of OKT4A Monoclonal Antibody On Cellular Immunity Of Nonhuman Primate Renal Allograft Recipients" *Transplantation*, vol. 53: 501–507, No. 3, Mar. 1992.

Thomas et al., "Promotion of Incompatible Allografts Acceptance In Rhesus Monkeys Given Posttransplant Antithymocyte Globulin And Donor Bone Marrow" *Transplantation*, vol. 47: 209–215, No. 2, Feb. 1989.

Thomas et al., "Veto Cells Induce Long–Term Kidney Allograft Tolerance In Primates Without Chronic Immunosuppression" *Transplantation Proceedings*, vol. 23: 11–13, No. 1 (Feb.) 1991.

Rayfield et al., "Tolerance, Immunocompetence, And Secondary Disease In Fully Allogeneic Radiation Chimeras" *Transplantation*, vol. 36: 183–189, No. 2, Aug. 1983.

* cited by examiner

INDUCED TOLERANCE TO XENOGRAFTS

This application is a continuation of application Ser. No. 07/838,595 filed on Feb. 19, 1992, now abandoned, which is a continuation-in-part of Sachs, et al., U.S. Ser. No. 07/817,761, filed on Jan. 8, 1992, now abandoned.

This invention was made with Government support under Contract #AI 31046, HL 18646, and HL 48049 awarded by the National Institutes of Health. The Government has certain rights in this invention.

BACKGROUND OF THE INVENTION

This invention relates to organ transplantation.

Organ procurement currently poses one of the major problems in organ transplantation, as the number of patients requiring transplants far exceeds the number of organs available. Xenotransplantation may provide a solution to this problem. Phylogenetically, non-human primates are the most closely related species to humans and might therefore represent the first choice as donors. In 1969, Reemtsma et al., achieved the first successful kidney human xenograft from a chimpanzee (Reetsma, K. et al., 1964, *Ann. Surg.* 160:384). However, the potential utilization of primate donors is limited by insufficient numbers, legal and ethical considerations, and the potential for transmitting dangerous viral diseases. Swine represent one of the few large animal species in which breeding characteristics make genetic experiments possible, making it possible to develop MHC homozygous lines of miniature swine. Miniature swine can be maintained at maximum adult weights of 200 to 300 lbs and are anatomically and physiologically close to humans. Therefore the organs of miniature swine might be appropriate for use as xenografts for human beings of all ages.

Tolerance to self major histocompatibility (MHC) antigens occurs during T cell maturation in the thymus (McDuffie et al., 1988, *J. Immunol.* 141:1840). Exposure of the immune system to MHC antigens during ontogeny can cause the immune system to lose reactivity to those antigens, thus leaving the animal specifically tolerant into adult life (Billingham et al., 1953, *Nature* 172:603). Transplantation immunologists have sought means of inducing tolerance in adult animals by production of lymphohematopoietic chimeras. The induction of tolerance across MHC barriers in adult mice by whole body irradiation (WBI) and bone marrow transplantation (BMT) has been studied extensively in murine models (Rayfield et al., 1983, Transplan. 36:183; Mayumi et al., 1989, *J. Exp. Med.* 169:213; Sykes et al., 1988, *Immunol. Today* 9:23).

The use of MHC mismatched BMT as a means of inducing tolerance to organ grafts can be accompanied by several major disadvantages: the preparative regimen involves lethal irradiation, with its inherent risks and toxicities; clinical applicability is limited by the fact that most potential recipients do not have an appropriate MHC-matched donor, and BMT across MHC barriers causes severe graft-vs-host-disease (GVHD). Removing the T lymphocytes in allogeneic bone marrow inocula (Rodt et al., 1971, *Eur. J. Immunol.* 4:25) to prevent GVHD is associated with increased rates of engraftment failure (Martin et al., 1988, *Bone Marrow Transplant* 3:445; O'Reilly et al., 1985, *Transplant. Proc.* 17:455; Soderling et al., 1985, *J. Immunol.* 135:941). While these drawbacks are generally considered acceptable for the treatment of otherwise lethal malignant diseases, they would severely limit the application of this methodology as a preparative regimen for organ transplantation, in which non-specific immunosuppressive agents, while not without major complications, are effective.

Use of a relatively non-toxic, non-myeloablative preparative regimen for bone marrow engraftment and specific transplantation tolerance has been applied to the concordant rat to mouse species combination (Sharabi, Y. et al., 1990, *J. Exp. Med.* 172:195–202). The treatment involved administration of monoclonal antibodies to eliminate mature T cell subsets (CD4 and CD8) as well as NK cells (NK1.1). These monoclonal antibodies permitted engraftment of xenogeneic bone marrow after only a sub-lethal (300 rads) dose of WBI and a local dose of 700 rads thymic irradiation. The resulting lymphoid reconstitution was superior to that of previously mixed xenogeneic chimeras prepared by lethal irradiation and reconstitution with mixtures of T cell-depleted syngeneic and xenogeneic bone marrow (Sharabi, Y., et al., 1990, *J. Exp. Med.* 172:195–202; Ildstad, et al., 1984, *Nature* 307:168–170) as recipients did not suffer toxic effects from the preparative regimen. In addition, attempts have been made to lengthen the survival of skin allografts in primates and man by intravenously administering a polyclonal preparation of horse anti-human antithymocyte globulin (ATG). The ATG was injected simultaneously with and on days immediately following grafting (Cosimi, A. B., et al., 1970. *Surgery.* 68:54–61).

In discordant species combinations, the humoral (antibody mediated) component of the immune system poses a major barrier. When primarily vascularized organs are grafted between discordant species, natural antibodies that recognize determinants expressed on the surfaces of vascular endothelial cells cause rejection of the organ within minutes of vascular anastomosis, due to activation of the complement and coagulation cascades (Hammer, C., et al., 1973, *Eur. Sug. Res.* 5:162; Hardy, M. A. et al, 1984, in S. Slavin, ed. Elsevier, B. V., p. 515). In attempts to prolong cardiac xenografts from pig donors, pre-existing natural antibodies have been absorbed from the blood of recipient primates by hemoperfusion of a donor-specific kidney (Cooper, D. K. C., et al. 1988, *J. Heart Transplan.* 7:238–246; Fischel, R. J., et al., 1990, *Transplant. Proc.* 22:1077).

SUMMARY OF THE INVENTION

In general, the invention features a method of inducing tolerance in a recipient mammal, e.g., a primate, e.g., a human, of a first species to a graft obtained from a mammal of a second species, e.g., a discordant species. The method includes: prior to or simultaneous with transplantation of the graft, introducing into the recipient mammal hematopoietic stem cells, e.g., bone marrow cells, or fetal liver or spleen cells, of the second species; (preferably, the hematopoietic stem cells home to a site in the recipient mammal); and prior to introducing the hematopoietic stem cells into the recipient mammal, introducing into the recipient mammal an antibody capable of binding to natural killer (NK) cells of the recipient mammal, to prevent NK mediated rejection of the hematopoietic cells. As will be explained in more detail below, the hematopoietic cells prepare the recipient for the graft that follows, by inducing tolerance at both the B-cell and T-cell levels. Preferably, hematopoietic cells are fetal liver or spleen, or bone marrow cells, including immature cells (i.e., undifferentiated hematopoietic stem cells; these desired cells can be separated out of the bone marrow prior to administration), or a complex bone marrow sample including such cells can be used.

One source of anti-NK antibody is anti-human thymocyte polyclonal anti-serum. As is discussed below preferably, a second, anti-mature T cell antibody can be administered as well, which lyses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Preferred embodiments include: the step of introducing into the recipient mammal, donor species-specific stromal tissue, preferably hematopoietic stromal tissue, e.g., fetal liver or thymus; and the step of prior to hematopoietic stem cell transplantation, introducing into the recipient mammal an antibody capable of binding to mature T cells of the recipient mammal.

Preferred embodiments include those in which: the same mammal of the second species is the donor of both the graft and the hematopoietic cells; the donor mammal is a swine, e.g., a miniature swine; the introduction is by intravenous injection; and the antibody is an anti-human thymocyte polyclonal anti-serum, obtained, e.g., from a horse or pig.

Preferred embodiments include: the step of prior to hematopoietic stem cell transplantation, irradiating the recipient mammal with low dose, e.g., between about 100 and 400 rads, whole body irradiation; and the step of prior to hematopoietic stem cell transplantation, irradiating the recipient mammal with, e.g., about 700 rads of thymic irradiation.

Preferred embodiments include: the step of prior to hematopoietic stem cell transplantation, absorbing natural antibodies from the blood of the recipient mammal by hemoperfusing an organ, e.g., a liver or a kidney, obtained from a mammal of the second species.

In another aspect, the invention features a method of inducing tolerance in a recipient mammal, e.g., a primate, e.g., a human to a graft obtained from a donor mammal of the same species. The method includes: prior to or simultaneous with transplantation of the graft, introducing into the recipient mammal hematopoietic stem cells, e.g., bone marrow cells or fetal liver or spleen cells, obtained from a mammal (preferably, the hematopoietic stem cells home to a site in the recipient mammal); prior to introducing the hematopoietic stem cells into the mammal, introducing into the mammal an antibody capable of binding to natural killer cells of the recipient mammal; prior to introducing the hematopoietic stem cells into the mammal, absorbing natural antibodies from the blood of the recipient mammal by hemoperfusing an organ obtained from a mammal of the same species; and prior to introducing the bone marrow into the mammal, irradiating the recipient mammal with low dose radiation to partially deplete the bone marrow of the mammal.

Preferred embodiments include: the step of introducing into the recipient mammal, donor species-specific stromal tissue, preferably hematopoietic stromal tissue, e.g., fetal liver or thymus; and prior to hematopoietic stem cell transplantation, introducing into the recipient mammal an antibody capable of binding to mature T cells of the recipient mammal.

Preferred embodiments include: the step of prior to hematopoietic stem cell transplantation, irradiating the recipient mammal with low dose, e.g., more than 100 rads and less than 400 rads, whole body irradiation; and the step of prior to hematopoietic stem cell transplantation, irradiating the recipient mammal with thymic irradiation, e.g., with about 700 rads.

Preferred embodiments include: the step of prior to hematopoietic stem cell transplantation, absorbing natural antibodies from the blood of the recipient mammal by hemoperfusing an organ, e.g., a liver or a kidney, obtained from a mammal of the second species.

In another aspect, the invention features a method of inducing tolerance in a recipient primate, e.g., a human, of a first species to a graft obtained from a mammal, e.g., a primate, of a second, preferably discordant, species. The method includes: introducing into the recipient primate donor species-specific stromal tissue; introducing into the recipient primate hematopoietic stem cells of the second species (preferably the hematopoietic stem cells, e.g., bone marrow cells or fetal liver or spleen cells, home to a site in the recipient primate); and introducing into the recipient primate an antibody capable of binding to natural killer cells of the recipient primate.

Preferred embodiments include those in which: the stromal tissue is introduced simultaneously with, or prior to, the hematopoietic stem cells; the hematopoietic stem cells are introduced simultaneously with, or prior to, the antibody; the stromal tissue is introduced simultaneously with, or prior to, the hematopoietic stem cells, and the hematopoietic stem cells are introduced simultaneously with, or prior to, the antibody.

Preferred embodiments include: and the step of prior to hematopoietic stem cell transplantation, introducing into the recipient mammal an antibody capable of binding to mature T cells of the recipient mammal.

Preferred embodiments include those in which: the same mammal of the second species is the donor of both the graft and the hematopoietic cells; the donor mammal is a swine, e.g., a miniature swine; the introduction is by intravenous injection; and the antibody is an anti-human thymocyte polyclonal anti-serum, obtained, e.g., from a horse or pig.

Preferred embodiments include: the step of prior to hematopoietic stem cell transplantation, irradiating the recipient mammal with low dose, e.g., between about 100 and 400 rads, whole body irradiation; and the step of prior to hematopoietic stem cell transplantation, irradiating the recipient mammal with, e.g., about 700 rads of thymic irradiation.

Preferred embodiments include: the step of prior to hematopoietic stem cell transplantation, absorbing natural antibodies from the blood of the recipient mammal by hemoperfusing an organ, e.g., a liver or a kidney, obtained from a mammal of the second species.

In another aspect the invention features a method of inducing tolerance in a recipient primate, e.g., a human to a graft obtained from a mammal of a second species. The method includes: introducing into the recipient primate donor species-specific hematopoietic stromal tissue; introducing into the recipient primate hematopoietic stem cells, e.g., bone marrow cells or fetal liver or spleen cells, of the second species (preferably the hematopoietic stem cells home to a site in the recipient primate); and introducing into the recipient primate a graft obtained from the mammal. Preferably the graft is obtained from a different organ than the hematopoietic stem cells.

Preferred embodiments include those in which: the stromal tissue is introduced simultaneously with, or prior to, the hematopoietic stem cells; the hematopoietic stem cells are introduced simultaneously with, or prior to, the graft; the stromal tissue is introduced simultaneously with, or prior to, the hematopoietic stem cells, and the hematopoietic stem cells are introduced simultaneously with, or prior to, the antibody.

Preferred embodiments include: and the step of prior to hematopoietic stem cell transplantation, introducing into the recipient mammal an antibody capable of binding to mature T cells of the recipient mammal.

Preferred embodiments include those in which: the same mammal of the second species is the donor of both the graft and the hematopoietic cells; the donor mammal is a swine, e.g., a miniature swine; the introduction is by intravenous injection; and the antibody is an anti-human thymocyte polyclonal anti-serum, obtained, e.g., from a horse or pig.

Preferred embodiments include: the step of prior to hematopoietic stem cell transplantation, irradiating the recipient mammal with low dose, e.g., between about 100 and 400 rads, whole body irradiation; and the step of prior to hematopoietic stem cell transplantation, irradiating the recipient mammal with, e.g., about 700 rads of thymic irradiation.

Preferred embodiments include: the step of prior to hematopoietic stem cell transplantation, absorbing natural antibodies from the blood of the recipient mammal by hemoperfusing an organ, e.g., a liver or a kidney, obtained from a mammal of the second species.

Preferred embodiments include those in which: the primate is a cynomolgus monkey; the primate is a human; the stromal tissue is fetal liver; the stromal tissue is thymus; the mammal is a swine; e.g., a miniature swine; the graft is a liver; the graft is a kidney.

"Tolerance", as used herein, refers to the inhibition of a graft recipient's ability to mount an immune response that would otherwise occur in response to the introduction of the graft. Tolerance can involve humoral, cellular, or both humoral and cellular, responses.

"A discordant species combination", as used herein, refers to two species in which hyperacute rejection occurs when vascular organs are grafted. Generally, discordant species are from different orders, while non-discordant species are from the same order. For example, rats and mice are non-discordant species, i.e. their MHC antigens are substantially similar, and they are members of the same order, rodentia.

"Hematopoietic stem cell", as used herein, refers to a cell that is capable of developing into mature myeloid and/or lymphoid cells.

"Miniature swine", as used herein, refers to partially inbred miniature swine.

"Graft", as used herein, refers to a body part, organ, tissue, cells, or portions thereof.

"Stromal tissue", as used herein, refers to the supporting tissue or matrix of an organ, as distinguished from its functional elements or parenchyma.

Methods of the invention avoid the undesirable side effects of broad spectrum immune suppressants which are often used in transplantation. Drugs such as Prednisone, Imuran, CyA, and, most recently, FK506, have all had an important impact on the field of transplantation. However, all of these drugs cause nonspecific suppression of the immune system, and therefore must be titrated carefully to avoid rejection while not completely eliminating immune function. Patients must stay on chronic immunosuppressive therapy for the remainder of their lives, facing the major complications of too much or too little immunosuppression, infection and rejection, respectively.

Other features and advantages of the invention will be apparent from the following detailed description, and from the claims.

DETAILED DESCRIPTION

The following procedure was designed to lengthen the time an implanted organ (a xenograft) survives in a xenogeneic host prior to rejection. The organ can be any organ, e.g., a liver, e.g., a kidney, e.g., a heart. The two main strategies are elimination of natural antibodies by organ perfusion, and transplantation of tolerance-inducing bone marrow. Thus, preparation of the recipient for transplantation includes any or all of the following steps. Preferably they are carried out in the following sequence.

First, a preparation of horse anti-human thymocyte globulin (ATG) is intravenously injected into the recipient. The antibody preparation eliminates mature T cells and natural killer cells. If not eliminated, mature T cells would promote rejection of both the bone marrow transplant and, after sensitization, the xenograft itself. Of equal importance, the ATG preparation also eliminates natural killer (NK) cells. NK cells probably have no effect on the implanted organ, but would act immediately to reject the newly introduced bone marrow. Anti-human ATG obtained from any mammalian host can also be used, e.g., ATG produced in pigs, although thus far preparations of pig ATG have been of lower titer than horse-derived ATG. ATG is superior to anti-NK monoclonal antibodies, as the latter are generally not lytic to all host NK cells, while the polyclonal mixture in ATG is capable of lysing all host NK cells. Anti-NK monoclonal antibodies can, however, be used.

The presence of donor antigen in the host thymus during the time when host T cells are regenerating post-transplant is critical for tolerizing host T cells. If donor hematopoietic stem cells are not able to become established in the host thymus and induce tolerance before host T cells regenerate repeated doses of anti-recipient T cell antibodies may be necessary throughout the non-myeloablative regimen. Continuous depletion of host T cells may be required for several weeks. Alternatively, e.g., if this approach is not successful, and tolerance (as measured by donor skin graft acceptance, specific cellular hyporesponsiveness in vitro, and humoral tolerance) is not induced in these animals, the approach can be modified to include host thymectomy. In thymectomized recipients, host T cells do not have an opportunity to differentiate in a host thymus, but must differentiate in the donor thymus. If this is not possible, then the animal has to rely on donor T cells developing in the donor thymus for immunocompetence. Immunocompetence can be measured by the ability to reject a non-donor type allogeneic donor skin graft, and to survive in a pathogen-containing environment.

It may also be necessary or desirable to splenectomize the recipient in order to avoid anemia.

Second, the recipient is administered low dose radiation in order to make room for newly injected bone marrow cells. A sublethal dose of between 100 rads and 400 rads whole body radiation, plus 700 rads of local thymic radiation, has been found effective for this purpose.

Third, natural antibodies are absorbed from the recipient's blood by hemoperfusion of a liver of the donor species. Pre-formed natural antibodies (nAb) are the primary agents of graft rejection. Natural antibodies bind to xenogeneic endothelial cells and are primarily of the IgM class. These antibodies are independent of any known previous exposure to antigens of the xenogeneic donor. B cells that produce these natural antibodies tend to be T cell-independent, and are normally tolerized to self antigen by exposure to these antigens during development. The mechanism by which newly developing B cells are tolerized is unknown. The liver is a more effective absorber of natural antibodies than the kidney.

The fourth step in the non-myeloablative procedure is to implant donor stromal tissue, preferably obtained from fetal liver, thymus, and/or fetal spleen, into the recipient, preferably in the kidney capsule. Stem cell engraftment and hematopoiesis across disparate species barriers is enhanced by providing a hematopoietic stromal environment from the donor species. The stromal matrix supplies species-specific factors that are required for interactions between hematopoietic cells and their stromal environment, such as hematopoietic growth factors, adhesion molecules, and their ligands.

As liver is the major site of hematopoiesis in the fetus, fetal liver can also serve as an alternative to bone marrow as a source of hematopoietic stem cells. The thymus is the major site of T cell maturation. Each organ includes an organ specific stromal matrix that can support differentiation of the respective undifferentiated stem cells implanted into the host. Although adult thymus may be used, fetal tissue obtained sufficiently early in gestation is preferred because it is free from mature T lymphocytes which can cause GVHD. Fetal tissues also tend to survive better than adult tissues when transplanted. As an added precaution against GVHD, thymic stromal tissue can be irradiated prior to transplantation, e.g., irradiated at 1000 rads. As an alternative or an adjunct to implantation, fetal liver cells can be administered in fluid suspension.

Finally, bone marrow cells (BMC), or another source of hematopoietic stem cells, e.g., a fetal liver suspension, of the donor are injected into the recipient. Donor BMC home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient several months after bone marrow chimerism has been induced, natural antibody against the donor will have disappeared, and the graft should be accepted by both the humoral and the cellular arms of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation. The use of xenogeneic donors allows the possibility of using bone marrow cells and organs from the same animal, or from genetically matched animals.

While any of these procedures may aid the survival of an implanted organ, best results are achieved when all steps are used in combination. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

In the case of xenogeneic grafts, the donor of the implant and the individual that supplies either the tolerance-inducing hematopoietic cells or the liver to be perfused should be the same individual or should be as closely related as possible. For example, it is preferable to derive implant tissue from a colony of donors that is highly inbred.

Detailed Protocol

In the following protocol for preparing a cynomolgus monkey for receipt of a kidney from a miniature swine donor, zero time is defined as the moment that the arterial and venous cannulas of the recipient are connected to the liver to be perfused.

On day -1 a commercial preparation (Upjohn) of horse anti-human anti-thymocyte globulin (ATG) is injected into the recipient. ATG eliminates mature T cells and natural killer cells that would otherwise cause rejection of the bone marrow cells used to induce tolerance. The recipient is anesthetized, an IV catheter is inserted into the recipient, and 6 ml of heparinized whole blood are removed before injection. The ATG preparation is then injected (50 mg/kg) intravenously. Six ml samples of heparinized whole blood are drawn for testing at time points of 30 min., 24 hrs and 48 hrs. Blood samples are analyzed for the effect of antibody treatment on natural killer cell activity (testing on K562 targets) and by FACS analysis for lymphocyte subpopulations, including CD4, CD8, CD3, CD11b, and CD16. Preliminary data from both assays indicate that both groups of cells are eliminated by the administration of ATG. If mature T cells and NK cells are not eliminated, ATG can be re-administered at later times in the procedure, both before and after organ transplantation.

Sublethal irradiation is administered to the recipient between days -1 and -8. Irradiation is necessary to eliminate enough of the recipient's endogenous BMC to stimulate hematopoiesis of the newly introduced foreign BMC. Sublethal total body irradiation is sufficient to permit engraftment with minimal toxic effects to the recipient. Whole body radiation (150 Rads) was administered to cynomolgus monkey recipients from a bilateral (TRBC) cobalt teletherapy unit at 10 Rads/min. Local irradiation of the thymus (700 Rads) was also employed in order to facilitate engraftment.

Natural antibodies are a primary cause of organ rejection. To remove natural antibodies from the recipient's circulation prior to transplantation, on day 0 an operative absorption of natural antibodies (nAB) is performed, using a miniature swine liver, as follows. At -90 minutes the swine donor is anesthetized, and the liver prepared for removal by standard operative procedures. At -60 minutes the recipient monkey is anesthetized. A peripheral IV catheter is inserted, and a 6 ml sample of whole blood is drawn. Through mid-line incision, the abdominal aorta and the vena cava are isolated. Silastic cannulas containing side ports for blood sampling are inserted into the blood vessels.

At -30 minutes the liver is perfused in situ until it turns pale, and then removed from the swine donor and placed into cold Ringers Lactate. The liver is kept cold until just prior to reperfusion in the monkey. A liver biopsy is taken. At -10 minutes the liver is perfused with warm albumin solution until the liver is warm (37 degrees).

At 0 time the arterial and venous cannulas of the recipient are connected to the portal vein and vena cava of the donor liver and perfusion is begun. Liver biopsies are taken at 30 minutes and 60 minutes, respectively. Samples of recipient blood are also drawn for serum at 30 minutes and 60 minutes respectively. At 60 minutes the liver is disconnected from the cannulas and the recipient's large blood vessels are repaired. The liver, having served its function of absorbing harmful natural antibodies from the recipient monkey, is discarded. Additional blood samples for serum are drawn from the recipient at 2, 24, and 48 hours. When this procedure was performed on two sequential perfusions of swine livers, the second liver showed no evidence of mild ischemic changes during perfusion. At the end of a 30 minute perfusion the second liver looked grossly normal and appeared to be functioning, as evidenced by a darkening of the venous outflow blood compared to the arterial inflow blood in the two adjacent cannulas. Tissue sections from the livers were normal, but immunofluorescent stains showed IgM on endothelial cells. Serum samples showed a decrease in natural antibodies.

To promote long-term survival of the implanted organ through T-cell and B-cell mediated tolerance, donor bone marrow cells are administered to the recipient to form chimeric bone marrow. The presence of donor antigens in the bone marrow allows newly developing B cells, and newly sensitized T cells, to recognize antigens of the donor as self, and thereby induces tolerance for the implanted organ from the donor. To stabilize the donor BMC, donor stromal tissue, in the form of tissue slices of fetal liver, thymus, and/or fetal spleen are transplanted under the kidney capsule of the recipient. Stromal tissue is preferably implanted simultaneously with, or prior to, administration of hematopoietic stem cells, e.g., BMC, or a fetal liver cell suspension.

To follow chimerism, two color flow cytometry can be used. This assay uses monoclonal antibodies to distinguish between donor class I major histocompatibility antigens and leukocyte common antigens versus recipient class I major histocompatibility antigens.

BMC can in turn be injected either simultaneously with, or preceding, organ transplant. Bone marrow is harvested and injected intravenously ($7.5 \times 10^8$/kg) as previously described (Pennington et al., 1988, *Transplantation* 45:21–26). Should natural antibodies be found to recur before tolerance is induced, and should these antibodies cause damage to the graft, the protocol can be modified to permit sufficient time following BMT for humoral tolerance to be established prior to organ grafting.

The approaches described above are designed to synergistically prevent the problem of transplant rejection. When a kidney is implanted into a cynomolgus monkey following liver absorption of natural antibodies, without use of bone marrow transplantation to induce tolerance, renal functions continued for 1–2 days before rejection of the kidney. When four steps of the procedure were performed (absorption of natural antibodies by liver perfusion, administration of ATG, sublethal irradiation and bone marrow infusion, followed by implant of a porcine kidney into a primate recipient), the kidney survived 7 days before rejection. Despite rejection of the transplanted organ, the recipient remained healthy.

When swine fetal liver and thymic stromal tissue were implanted under the kidney capsule of two sublethally irradiated SCID mice, 25–50% of peripheral blood leukocytes were of donor lineage two weeks post-transplantation. A significant degree of chimerism was not detected in a third animal receiving fetal liver without thymus. These procedures did not employ any chemical immunosuppressants.

Other Embodiments

Other embodiments are within the following claims.

For example, implanted grafts may consist of organs such as liver, kidney, heart; body parts such as bone or skeletal matrix; tissue such as skin, intestines, endocrine glands; or progenitor stem cells of various types.

The methods of the invention may be employed with other mammalian recipients (e.g., rhesus monkeys, humans) and may use other mammalian donors (e.g., primates, swine, sheep, dogs).

The methods of the invention may be employed in combination, as described, or in part.

The method of introducing bone marrow cells may be altered, particularly by (1) increasing the time interval between injecting hematopoietic stem cells and implanting the graft; (2) increasing or decreasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension may be used; or (6) varying the donor source of hematopoietic stem cells. Although hematopoietic stem cells derived from the graft donor are preferable, hematopoietic stem cells may be obtained from other individuals or species, or from genetically-engineered inbred donor strains, or from in vitro cell culture.

Methods of preparing the recipient for transplant of hematopoietic stem cells may be varied. For instance, the recipient may undergo a splenectomy or a thymectomy. The latter would preferably by administered prior to the non-myeloablative regimen, e.g., at day -14.

Hemoperfusion of natural antibodies may: (1) make use of other vascular organs, e.g., liver, kidney, intestines; (2) make use of multiple sequential organs; (3) vary the length of time each organ is perfused; (4) vary the donor of the perfused organ. Irradiation of the recipient may make use of: (1) varying the absorbed dose of whole body radiation below the sublethal range; (2) targeting different body parts (e.g., thymus, spleen); (3) varying the rate of irradiation (e.g., 10 rads/min, 15 rads/min); or (4) varying the time interval between irradiation and transplant of hematopoietic stem cells; any time interval between 1 and 14 days can be used, and certain advantages may flow from use of a time interval of 4–7 days. Antibodies introduced prior to hematopoietic cell transplant may be varied by: (1) using monoclonal antibodies to T cell subsets or NK cells (e.g., anti-NKH1$_A$, as described by U.S. Pat. No. 4,772,552 to Hercend, et al., hereby incorporated by reference); (2) preparing anti-human ATG in other mammalian hosts (e.g., monkey, pig, rabbit, dog); or (3) using anti-monkey ATG prepared in any of the above mentioned hosts.

As an alternative or adjunct to hemoperfusion, host antibodies can be depleted by administration of an excess of hematopoietic cells.

Stromal tissue introduced prior to hematopoietic cell transplant, e.g., BMT, may be varied by: (1) administering the fetal liver and thymus tissue as a fluid cell suspension; (2) administering fetal liver or thymus stromal tissue but not both; (3) placing a stromal implant into other encapsulated, well-vascularized sites; or (4) using adult thymus or fetal spleen as a source of stromal tissue.

Other embodiments are within the following claims.

What is claimed is:

1. A method of inducing xenogeneic tolerance in a recipient primate to a swine graft comprising:

introducing into said recipient primate an antibody preparation which eliminates mature T cells and NK cells of said recipient primate;

irradiating said recipient primate with low dose irradiation, said irradiation being non-myeloablative and being sufficient to partially deplete said recipient primate's endogenous bone marrow cells in order to stimulate hematopoiesis of newly introduced swine hematopoietic stem cells;

removing natural anti-xenogeneic antibodies from the blood of said recipient;

introducing into said recipient primate a preparation which comprises donor swine hematopoietic stem cells which develop into mature myeloid or lymphoid cells, or both, and which form a chimeric lymphohematopoietic population in said recipient primate, thereby inducing immunological tolerance in said recipient primate to a swine graft; and introducing into the recipient primate a swine graft, wherein the same swine, a genetically matched swine, or a swine from a highly inbred herd, is the donor of both the graft and the hematopoietic cells.

2. The method of claim 1, wherein said antibody preparation comprises an anti-human thymocyte polyclonal antiserum.

3. The method of claim 1, wherein said graft is obtained from a different organ than the hematopoietic stem cells.

4. The method of claim 1, wherein said hematopoietic stem cells are fetal liver or spleen cells.

5. The method of claim 1, wherein said hematopoietic stem cells are bone marrow cells.

6. The method of claim 1, wherein said swine graft is a liver.

7. The method of claim 1, wherein said swine graft is a kidney.

8. The method of claim 1, wherein the donor of both the graft and the hematopoietic cells is the same swine.

9. The method of claim 1, wherein the donor of both the graft and the hematopoietic cells is a genetically matched swine.

10. The method of claim 1, wherein the donor of both the graft and the hematopoietic cells is a swine from a highly inbred herd.

11. The method of claim 1, wherein said recipient primate is a human.

12. The method of claim 1, wherein said swine is a miniature swine.

13. The method of claim 1, wherein said recipient primate is a human and said swine is a miniature swine.

14. The method of claim 1, wherein said low dose irradiation is more than 100 rads and less than 400 rads.

15. The method of claim 1, further comprising in addition to said low dose irradiation, and prior to hematopoietic stem cell transplantation, irradiating the recipient primate with thymic irradiation.

16. The method of claim 15, wherein said thymic irradiation is 700 rads.

17. The method of claim 1, wherein the step of removing natural anti-xenogeneic antibodies comprises adsorbing natural antibodies from the blood of said recipient primate by hemoperfusing an organ obtained from a swine.

18. The method of claim 17, wherein said organ is a liver.

19. The method of claim 17, wherein said organ is a kidney.

20. The method of claim 1, further comprising introducing a second administration of said preparation which comprises hematopoietic stem calls into said recipient primate.

21. The method of claim 1, further comprising introducing into said recipient primate swine stromal tissue.

22. The method of claim 13, wherein the donor of both the graft and the hematopoietic cells is a swine from a highly inbred herd.

23. The method of claim 22, wherein said swine graft is a kidney.

24. The method of claim 22, wherein said swine graft is a liver.

* * * * *